United States Patent [19]

Gonser

[11] 3,961,630
[45] June 8, 1976

[54] PROTECTIVE CIRCUIT FOR RADIO-FREQUENCY ELECTROSURGICAL DEVICE

[75] Inventor: Donald I. Gonser, Forest Park, Ohio

[73] Assignee: Dentsply Research & Development Corporation, Milford, Del.

[22] Filed: Dec. 5, 1974

[21] Appl. No.: 529,608

Related U.S. Application Data

[62] Division of Ser. No. 414,646, Nov. 12, 1973, Pat. No. 3,870,047.

[52] U.S. Cl. ............... 128/303.14; 128/303.17
[51] Int. Cl.² ............... A61B 17/36; A61N 3/02
[58] Field of Search ............... 128/303.14, 303.13, 128/303.17, 303.18, 2.1 P, 419 R–422; 317/12 R, 12 A, 16

[56] References Cited
UNITED STATES PATENTS

| | | | |
|---|---|---|---|
| 3,058,470 | 10/1962 | Seeliger et al. | 128/303.17 |
| 3,675,655 | 7/1972 | Sittner | 128/303.17 |
| 3,707,149 | 12/1972 | Hao et al. | 128/303.14 |
| 3,730,188 | 5/1973 | Ellman | 128/303.14 |

FOREIGN PATENTS OR APPLICATIONS

| | | | |
|---|---|---|---|
| 1,128,769 | 1/1957 | France | 128/303.17 |
| 855,459 | 11/1960 | United Kingdom | 128/303.17 |
| 166,452 | 11/1964 | U.S.S.R. | 128/303.17 |

*Primary Examiner*—Dalton L. Truluck
*Assistant Examiner*—Lee S. Cohen
*Attorney, Agent, or Firm*—James W. Pearce; Roy F. Schaeperklaus

[57] ABSTRACT

An electrosurgical device in which high frequency electrical energy powers a cutting electrode. Radio frequency energy is set up in a driver coil and a driven coil mounted in a handpiece. The driver coil energizes the driven coil to energize a surgical electrode connected to one end of the driven coil. Connection between the source of radio frequency energy and the driver coil includes a circuit in which condensers and impedances are so connected that, if there is a failure of the condensers, energy is dissipated.

4 Claims, 10 Drawing Figures

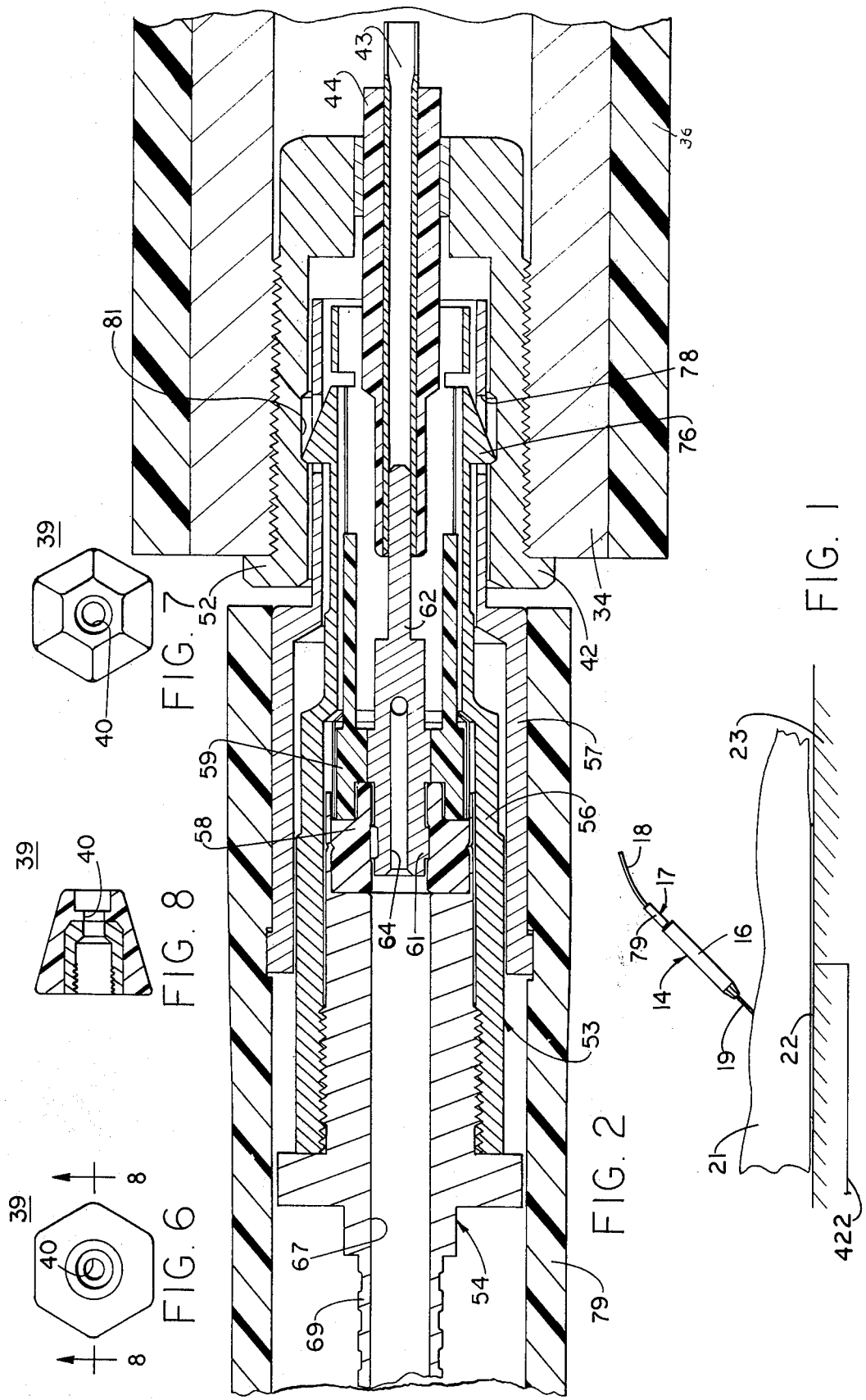

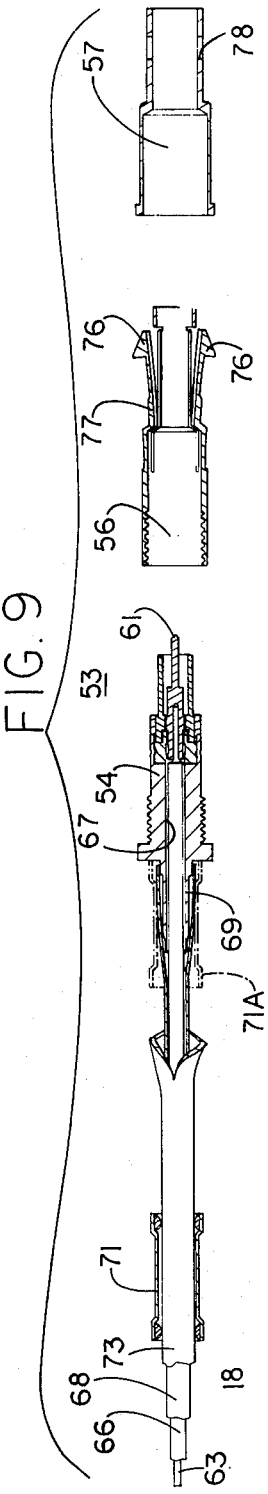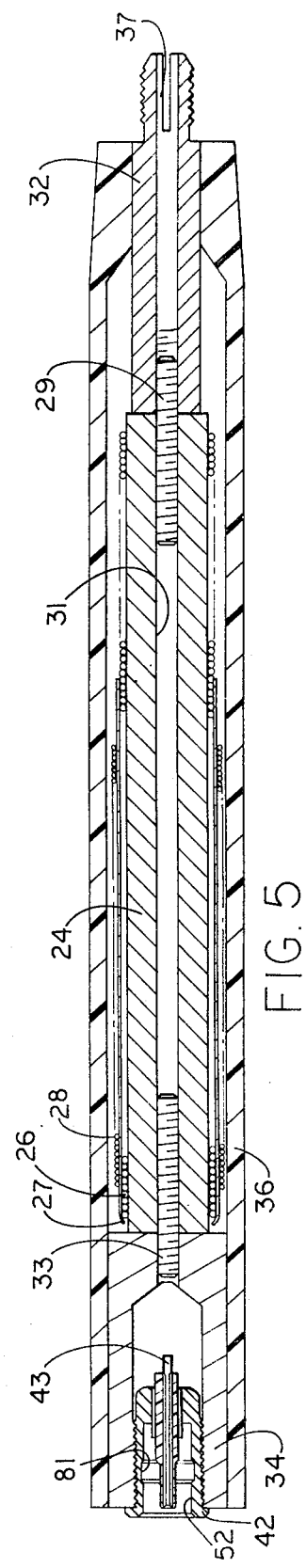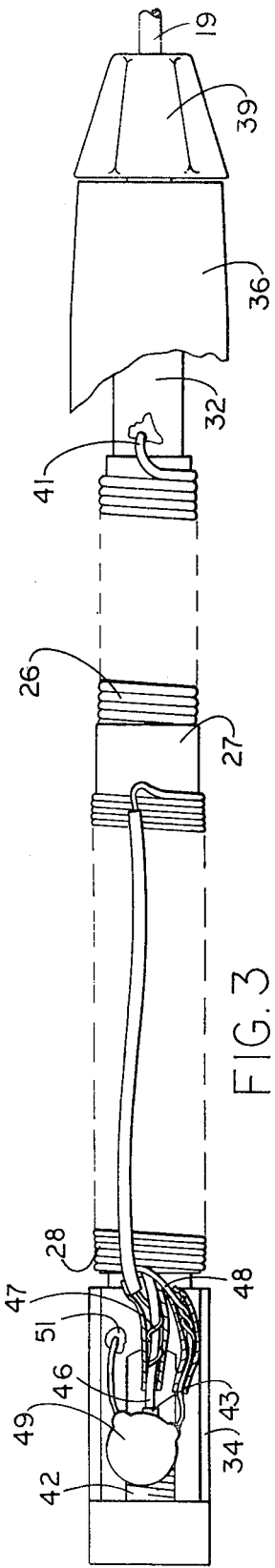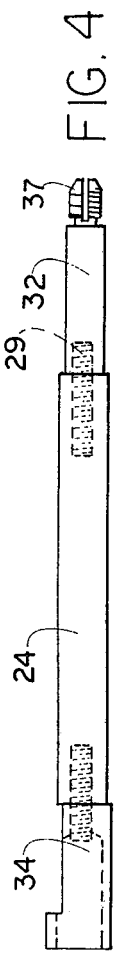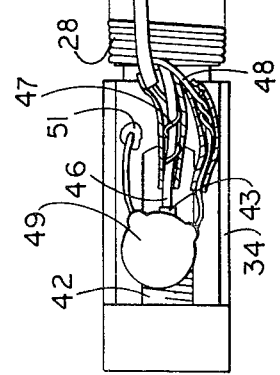

PROTECTIVE CIRCUIT FOR RADIO-FREQUENCY ELECTROSURGICAL DEVICE

This is a division of my copending application Ser. No. 414,646, filed Nov. 12, 1973, now U.S. Pat. No. 3,870,047.

This invention relates to an electrosurgical device. More particularly, this invention relates to a multi-purpose electrosurgical device. The device of this invention represents an improvement in the type of device shown in my copending application Ser. No. 310,830, filed Nov. 30, 1972, U.S. Pat. No. 3,804,096 issued Apr. 16, 1974.

An object of this invention is to provide a radio frequency electrosurgical device in which a surgical electrode can be energized by a handpiece coil connected thereto, which handpiece coil, in turn, is energized by a driver coil coupled thereto, the radio frequency energy being supplied through a transmission line from a radio frequency power source.

A further object of this invention is to provide such a device which develops both a cutting current and a coagulating current and which provides a sonic warning signal of one frequency when the cutting current is being produced and a sonic warning signal of a different frequency when the coagulating current is being produced.

A further object of this invention is to provide such a device which also develops a blended current and which provides a sonic warning signal which is a blend of the frequencies when the blended current is being developed.

A further object of this invention is to provide such a device in whch radio-frequency electrosurgical current is fed to an electrosurgical instrument through condensers in series between a power source and the instrument, and means is provided between condensers for bleeding of non-radio-frequency current to ground in the event of condenser failure.

Briefly, this invention provides an electrosurgical device including a handpiece in which a first coil and a second coil are wound on a handpiece core. A source of radio-frequency current of an electrosurgical frequency is coupled to one end of the second coil and an electrode is connected to one end of the first coil. The source of radio-frequency current is coupled to the second coil through series connected condensers, and inductance means is provided between condensers to bleed off non-radio-frequency current to ground in the event of condenser failure. The power source has means for generating cutting current, coagulating current, and blended current. Sonic warning devices of different frequencies sound when the cutting and coagulating currents are being generated. A blend sound is produced when a blended current is generated.

The above and other objects and features of the invention will be apparent to those skilled in the art to which this invention pertains from the following detailed description and the drawings in which:

FIG. 1 is a view in side elevation of an electrosurgical device constructed in accordance with an embodiment of this invention, the device being shown in association with a fragmentary portion of a patient on a fragmentary portion of a table, the table being shown in section;

FIG. 2 is an enlarged fragmentary view in lengthwise section of the electrosurgical device shown in FIG. 1, wiring being omitted for clarity;

FIG. 3 is a plan view of a handpiece portion of the electrosurgical device, a case thereof being broken away to reveal interior construction;

FIG. 4 is a view in side elevation of an inner assembly of the handpiece portion;

FIG. 5 is a view in lengthwise section of the handpiece portion shown in FIG. 3, wiring thereof being broken away to reveal structural details;

FIG. 6 is a view in end elevation of a cap of the device;

FIG. 7 is another end elevational view of the cap shown in FIG. 6;

FIG. 8 is a view in section taken on the line 8—8 in FIG. 6;

FIG. 9 is an exploded view of a power cable of the electrosurgical device and end fastener elements thereof.

In the following detailed description and the drawings, like reference characters indicate like parts.

Figure 10:
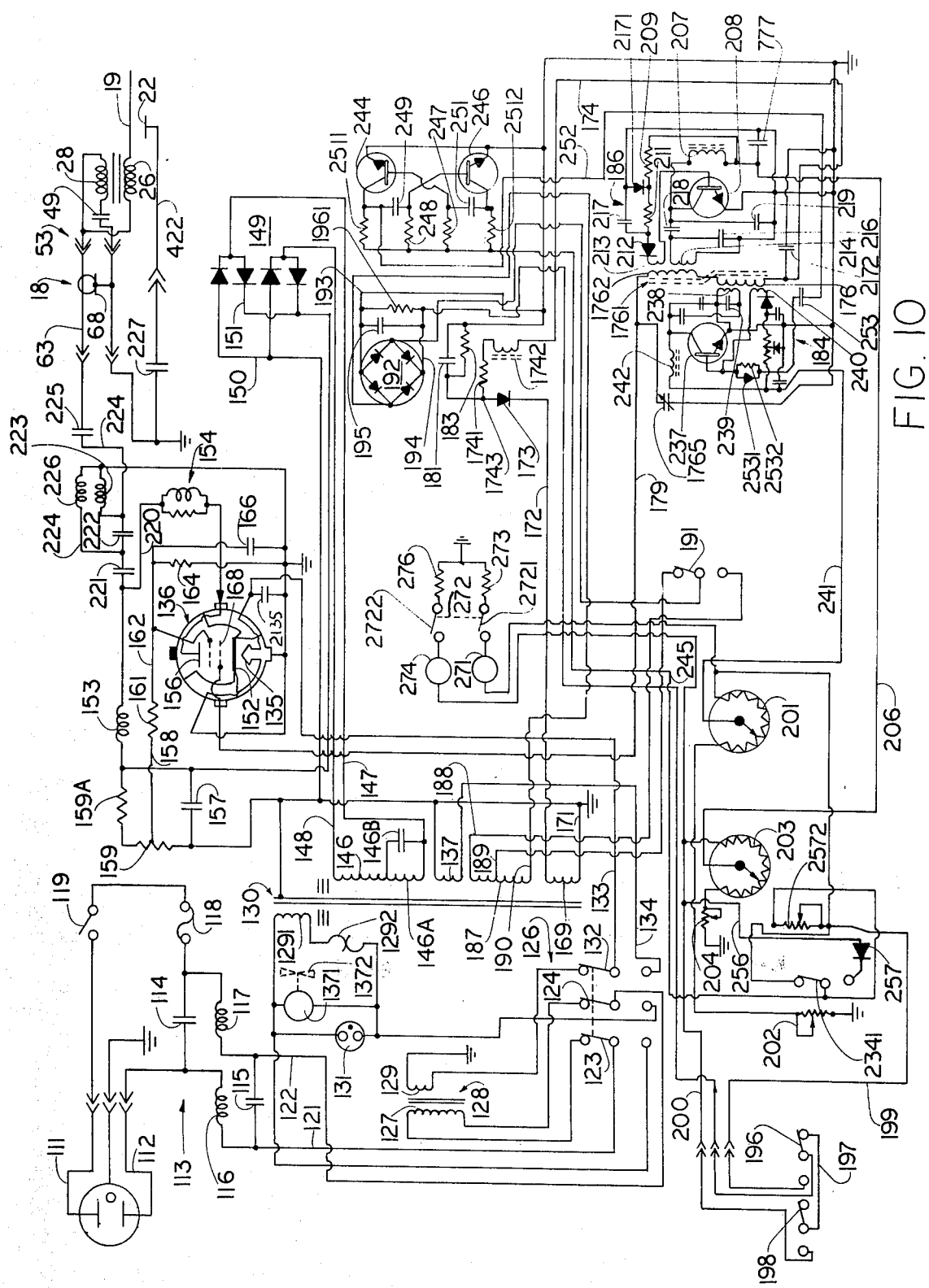
FIG. 10 is a schematic circuit diagram of the device.

In FIG. 1 is shown an electrosurgical device 14 constructed in accordance with an embodiment of this invention. The device 14 includes a handpiece portion 16 and a cable connecting portion 17. The cable connecting portion 17 is mounted on an end of a coaxial cable 18. The handpiece portion 16 is arranged to support a surgical electrode 19. In FIG. 1 the surgical electrode is shown in position to perform a surgical operation on a patient 21. The patient is shown in position on a passive electrode 22 and supported by a table 23 which underlies the passive electrode 22. The passive electrode 22 is provided with a lead 422.

The handpiece portion 16 (FIG. 5) includes a central tubular electromagnetic core 24. A first or driven coil 26 is wound on the core 24. A layer of insulation 27 overlies the first coil, and a second or driver coil 28 is wound on the layer of insulation. A stud 29, which is mounted in a central bore 31 of the core 24, supports a hollow chuck fitting 32. A second stud 33 mounted in the central bore 31 supports a hollow receptacle sleeve fitting 34. A hollow sleeve 36 of dielectric material surrounds the receptacle sleeve fitting 34, the coils 26 and 28, and the chuck fitting 32 with chuck jaws 37 of the fitting 32 extending outwardly thereof. The surgical electrode 19 can be received inside the chuck jaws 37. A cap 39 (FIGS. 3 and 6–8) is threaded on the chuck jaws 37 and can tighten the chuck jaws on the electrode 19. The cap 39 has a central opening 40 through which the electrode 19 projects. One end portion 41 (FIG. 3) of the first coil 26 is attached to the chuck fitting 32 as by soldering so that the end portion 41 of the first coil 26 is electrically connected to the electrode 19.

A cable connector receptacle 42 is mounted in the receptacle sleeve fitting 34. As shown in FIG. 2, the cable connector receptacle 42 includes a central tube 43, which is supported by an insulator sleeve 44. The other end portion 46 of the first coil 26 is attached to the tube 43 as shown in FIG. 3. One end portion 47 of the second coil 28 is soldered to the end portion 46 of the coil 26. The other end portion 48 of the second coil 28 is attached to one side of a capacitor 49. The other side of the capacitor 49 is attached to the receptacle sleeve fitting 34 by solder as indicated at 51.

The cable connector receptacle 42 is provided with a central socket 52 (FIG. 5) which can receive a coaxial cable end assembly 53. The coaxial cable end assembly 53 includes a body 54 (FIGS. 2 and 9), an annular latch member 56, and an annular latch actuator member 57.

The body 54 supports annular insulator members 58 and 59 (FIG. 2) inside which is mounted a contact member 61 having a head 62 which can be received inside the central tube 43 in electrical connection therewith. A central lead 63 (FIG. 9) of the coaxial cable 18 can be received inside a socket 64 (FIG. 2) in the contact member 61 with an insulating layer 66 (FIG. 9) of the coaxial cable 18 being received inside a central bore 67 of the body 54. An end portion of an annular conductor 68 of the coaxial cable 18 overlies a stem 69 of the body 54 to form an electrical connection therewith. A sleeve 71, which surrounds the cable 18, can be advanced to the position shown in dot-dash lines at 71A to hold the annular conductor 68 in position on the stem 69. An outer insulation sleeve 73 forms an outer layer of the coaxial cable 18 surrounding the annular conductor 68.

The latch member 56 is threaded on the body 54 and includes latch hooks 76 mounted on spring arms 77 which resliently urge the latch hooks 76 outwardly. The latch actuator 57 is slideably mounted on the latch member 56. The latch actuator 57 includes slots 78 through which the hooks 76 extend. A sleeve 79 (FIG. 2) of insulating material is mounted on the latch actuator member 57. When the assembly 53 is mounted in the central socket 52, the teeth 76 extend into an annular slot 81 (FIG. 2) in the wall of the socket 52 to lock the assembly 53 in the socket 52. When the insulation sleeve 79 and the latch actuator 57 are moved to the left as shown in FIG. 2, the teeth 76 are urged inwardly to cause release of the teeth 76 from the slot 81 to permit removal of the cable end assembly 53.

In FIG. 10 is shown schematically the wiring diagram of the device. Alternating current power is supplied by power leads 111 and 112. A power line radio frequency interference filter 113 including condensers 114 and 115 and inductances 116 and 117 greatly attenuates radio frequency feed-back to the power leads. A power line fuse 118 is provided in the lead 111. An interlock switch 119 can be provided in the power lead 111. The interlock switch 119 is closed during operation of the device but can be arranged to open when a casing of the device (not shown) is opened.

Leads 121 and 122 from the power line filter 113 are connected to poles 123 and 124, respectively, of a triple pole double throw on-off switch 126. When the on-off switch 126 is in the position shown (off position), the leads 121 and 122 are connected to power a primary winding 127 of a transformer 128 to impress a low voltage such as 4 volts on a secondary winding 129 thereof. When the on-off switch 126 is in its other position (on position), the leads 121 and 122 are connected to a primary winding 1291 of a transformer 130 to power the transformer. A panel light 131 is connected in parallel with the primary winding 1291 to indicate that the primary winding 1291 is powdered. A thermally activated circuit breaker 1292 in series with the primary winding 1291 protects the transformer 130. A third pole 132 of the switch 126, when in the on position, connects leads 133 and 134 to connect one side of a heater electrode 135 of a tetrode main power amplifier tube 136 to one side of a first secondary winding 137 of the transformer 130, which can be constructed to produce approximately 6 volts AC to the heater electrode 135. A capacitor 2135 is connected between the line 133 and ground to shunt any radio-frequency current from the heater electrode 135. The other side of the first secondary winding 137 is connected to ground as is the opposite side of the heater electrode 135. A fan motor 1371 is also connected in parallel with the primary winding 1291 to drive a fan 1372 which blows air on the tetrode 136 and other components to cool the tetrode and other components. When the on-off switch 126 is swung to its off position, the pole 132 connects the lead 133 to the secondary winding 129 of the transformer 128 so that the heater electrode 135 is heated not only when the on-off switch 126 is in the on position but also when the on-off switch 126 is in the off position. As already pointed out, the secondary winding 129 of the transformer 128 can be arranged to deliver about four volts so that the heater electrode 135 is heated but at a lower temperature when the switch 126 is in the off position but is maintained at a sufficient temperature that the device will operate at once when the switch 126 is turned on.

A secondary winding 146 of the transformer 130 supplies a voltage of approximately 2000 volts AC across leads 147 and 148 to a full wave bridge rectifier 149 which supplies 2000 volts direct current across leads 150 and 151. The lead 150 is connected to ground as is a cathode 152 of the tetrode 136. The lead 151 is connected through a plate choke 153 and a parasitic suppressor network 154 to a plate 156 of the tetrode 136 so that 2000 volts DC is impressed between the cathode 152 and the plate 156 of the tetrode 136. A filter condenser 157 smooths out wave form ripple from the rectifier 149. A tapped resistor 159 and a fixed resistor 159A are connected in series across the leads 150 and 151. A lead 158 connected to the tap of the tapped resistor 159 supplies a positive potential through resistor 161 and a lead 162 to a screen grid of the tetrode 136. A voltage of approximately 380 volts can be taken off at the tap which is maintained on the screen grid. An appropriate resistance 164 bleeds off screen grid current to ground. A capacitor 166 connected between the screen grid lead 162 and ground removes or shunts out radio frequency from the screen grid.

A section 146A of the second secondary winding 146 of the transformer 130 is connected in parallel with a capacitor 146B to form a tuned circuit tuned to a line input frequency, which can be 60 Hertz, to stabilize the secondary winding voltages to a variation of approximately ±1% with a change in input voltage of ±10% impressed on the primary winding 129. Thus, the transformer 130 is a substantially constant voltage transformer stabilizing all the circuitry of the device.

A bias voltage for a control grid 168 of the tetrode 136 is supplied by a third secondary winding 169 of the transformer 130. A first lead 171 from the winding 169 is connected to ground and a second lead 172 from the winding 169 is connected to a rectifier 173. The rectifier 173 supplies a negative potential through a resistance 1741 and an inductance 1742 to a lead 174, which is connected to one end of a first series winding 176 of a transformer 1761. The other end of the winding 176 is connected through a second series winding 1762 of the transformer 1761 to a lead 179 connected to the control grid 168 of the tetrode 136. A condenser 181 which is connected between ground and a junction 1743 smooths out the wave form of the potential from the rectifier 173. A resistance 183 connected in parallel with the condenser 181 serves to discharge the condenser 181 when the device is turned off. The bias voltage can be approximately −120 volts.

Oscillator circuits 184 and 186 for the device are powered from a fourth secondary winding 187 of the transformer 130. Leads 188, 189 and 190 from the winding 187 are connected through a single pole double throw switch 191 to a full wave bridge rectifier 192 which supplies a DC voltage across leads 193 and 194. When the switch 191 is in the position shown, a voltage of approximately 16 volts is supplied across the leads 193 and 194. When the switch 191 is in its other position, a voltage of approximately 25 volts is supplied across the leads 193 and 194. A condenser 195 connected across leads 193 and 194 smooths ripple voltage. A resistance 1961 connected across the leads 193 and 194 discharges the condenser 195 when the device is turned off. The lead 193 is connected to ground. The lead 194 is connected to the pole of a single pole double throw switch 196. When the switch 196 is in the position shown, the lead 194 is connected through a short lead 197 to the pole of a single pole double throw switch 198. The switches 196 and 198 can be foot operated switches. The switches 196 and 198 are shown in their normal positions. When the switch 196 is turned to its other position, the lead 194 is connected to a lead 199. When the switch 198 is turned to its other position, while the switch 196 remains in the position shown, the lead 194 is connected to lead 200. If the switches 196 and 198 are both turned to their other position, the lead 194 is connected to the lead 199, and it is impossible to connect both the leads 199 and 200 to the lead 194 at the same time. The lead 199 is connected to one side of a potentiometer 201. The other side of the potentiometer 201 is connected to ground through an adjustable resistor 202. In a similar manner, the lead 200 is connected to one side of a potentiometer 203. The other side of the potentiometer 203 is connected to ground through an adjustable resistor 204. Thus, when the switch 196 is advanced to its other position, a selected DC voltage is impressed across the potentiometer 201 and when the switch 198 is advanced to its other position while the switch 196 remains in the position shown, a selected DC voltage is impressed across the potentiometer 203.

A voltage between zero and the selected voltage is impressed upon a lead 206 connected to the tap of the potentiometer 203 when the switch 198 is in its other position and the switch 196 is in the position shown. The lead 206 is connected through an inductance or choke 207 to the collector of a transistor 208, which is a part of the oscillator circuit 186. The emitter of the transistor 208 is connected to ground. The lead 206 is also connected through resistors 209 and 211 and a rectifier 212 to one side of a tickler coil 213. The rectifier 212 functions to reverse bias the base of the transistor 208 and is connected to one side of the tickler coil 213, which is excited by a tank circuit consisting of an inductance 214 and a condenser 216 coupled to the transistor 208 in which continuous oscillation is set up by the tank circuit. The other side of the tickler coil 213 is connected to the base of the transistor 208. The rectifier 212 establishes the reverse bias required by the base of the transistor 208 and is also connected to ground through a condenser 217 which establishes the bias network circuitry. A bias rectifier 2171 is connected between ground and a junction between the resistors 209 and 211. The tank circuit is connected with the collector of the transistor 208 through a coupling condenser 218. A condenser 219 is connected between the emitter and the collector of the transistor 208 to shunt out radio frequency potentials. A capacitor 777 acts to provide a bypass to ground shunt for attenuating radio frequency feed-back into the line 206 when the oscillating circuit 186 is in operation. The tank circuit can be tuned to oscillate at a rate of approximately 1.8 megaHertz. The oscillation is picked up by the transformer winding 1762 and the voltage thereof is multiplied by the transformer winding and impressed by way of the lead 179 on the control grid 168 of the tetrode 136 to provide an amplified output by the tetrode 136 of that frequency. The output of the tetrode 136 is impressed by way of a lead 220 on an output circuit which is coupled through condenser 221 to a tuned pie network which includes condensers 222 and 225 and inductances 223 and 226. Right-hand ends of the inductances 223 and 226 are connected to ground so that, if there should be failure of the condensers 221 and 222, the direct current output of the tetrode 136 would be drained off to ground without danger to the patient. A take-off lead 224 which is connected between the condenser 222 and the inductance 223 extends to one side of a condenser 225. The other side of the condenser 225 is connected to the central lead 63 of the coaxial cable 18 and through the cable end assembly 53 to one end of the second coil 28. The annular conductor 68 of the coaxial cable 18 is connected to ground. The passive electrode 22 is connected to one side of a condenser 227. The other side of the condenser 227 is connected to ground. Thus, a continuous radio frequency oscillating potential is set up in the first coil 26 and in the electrode 19.

When the switch 198 is moved to its other position and the switch 196 remains in the position shown and a single pole double throw blend switch 2341 is in the off position shown, a continuous oscillation is impressed on the coil 28. When the switch 196 is moved to its other position and while the single pole double throw blend switch 2341 is in the off position shown, the oscillating circuit 184 is energized to produce an interrupted oscillation in the driver coil 28. The oscillating circuit 184 is generally similar to the circuit 186 already described and includes a transistor 237, a tank circuit inductance 238, a tank circuit capacitor 239, and a tickler coil 240 and associated elements. A lead 241, which is connected to the tap of the potentiometer 201, is connected through a choke 242 to the collector of the transistor 237. Moving of the switch 196 to its other position impresses a selected DC voltage across the potentiometer 201 and a DC voltage between zero and the selected voltage is impressed upon the lead 241. The emitter of the transistor 237 is connected to ground. The oscillating circuit 184 is set in operation to deliver an oscillator frequency of approximately 1.8 megaHertz on the control grid of the tetrode 136. The lead 199, which is connected to the high side of the potentiometer 201, is also connected through the pole of the blend switch 2341 to a lead 245, which is connected to base leads of transistors 244 and 246, which form a multivibrator circuit, through resistors 247 and 248, respectively. The collector lead of the transistor 244 is coupled through a condenser 249 to the base of the transistor 246 and the collector of the transistor 246 is coupled through a condenser 251 to the base of the transistor 244. The collectors of the transistors 244 and 246 are connected to the lead 245 through resistors 2511 and 2512, respectively. Emitters of the transistors 244 and 246 are connected to ground. The multivibrator circuit can be arranged to oscillate at a rate of approximately 7000 Hertz. A lead 252 from the collector of the transistor 244 is connected through a coupling condenser 253 and a rectifier 2531, and a resistor 2532 connected in parallel with the rectifier 2531, to the base of the transistor 237 so that the operation of the oscillating circuit 184 is interrupted at a rate of 7000 Hertz to put an interrupted oscillating potential on the control grid of the tetrode 136 and to supply an interrupted radio-frequency oscillating potential at the electrode 19. The rectifier 2531 and the resistor 2532 connected in parallel with the rectifier 2531 forms a network which preserves the wave form generated by the multivibrator circuit as it is transmitted to the oscillator circuit 184.

An adjustable capacitor 1765 is connected between the lead 179 and ground and can be adjusted so that it tunes with the transformer secondary coils 176 and 1762 and with the capacitor 2172 so that the grid input is tuned with the plate series tuned circui 222, 223, 225, and 226. Both of these circuits are tuned with the driver input oscillating circuits 184 and 186 at approximately 1.8 megaHertz.

When the blend switch 2341 is disposed in its other or "on" position, moving of the switch 198 to its other position while the switch 196 is in the position shown energizes both of the oscillating circuits 184 and 186. The oscillating circuit 186 is energized in the same manner as already described. The lead 200, which is connected to the switch 198, is connected through a lead 256, a rectifier 257, the blend switch 2341, the lead 245, and an adjustable resistor 2572 to the lead 199, which is connected to the right hand end of the potentiometer 201. The rectifier 257 prevents unwanted cross feed between the leads 199 and 200. Both the oscillating circuit 184 and the oscillating circuit 186 are set in operation and an output is provided from the tetrode 136 for energizing the electrode 19 which combines the interrupted oscillation of the circuit 184 with the uninterrupted oscillation of the circuit 186.

The lead 199, which is connected to the high side of the potentiometer 201, is also connected to a sonic signalling device 271, which is constructed to produce a sound signal of a selected frequency, which can be 2900 Hz. The sonic signalling device 271 is connected to ground through a pole 2721 of an on-off switch 272 and a resistor 273. Similarly, the lead 200, which is connected to the high side of the potentiometer 203, is also connected to a second sonic signalling device 274, which is constructed to produce a sound signal of a second selected frequency, which can be 4500 Hz. The sonic signalling device 274 is connected to ground through a pole 2722 of the on-off switch 272 and a resistor 276. The sonic signalling device 271 sounds when the potentiometer 201 is energized to energize the oscillating circuit 184 to produce a sound signal which indicates to the user of the device that the oscillating circuit 184 is operating. The sonic signalling device 274 similarly produces a sound signal when the oscillating circuit 186 is energized to indicate that the oscillating circuit 186 is operating. When both the oscillating circuits 184 and 186 are operating, i.e., when a blended current is being produced, a sound signal is produced which is a blend of the selected frequencies. If the user does not want sound signals, the on-off switch 272 can be opened. The size of the resistors 273 and 276 determines the loudness of the sound signals.

When the device is to be used, an appropriate electrode 19 is mounted in the chuck jaws 37 (FIG. 5). The blend switch 2341 (FIG. 10) is disposed either in its other position at which a blend of interrupted and uninterrupted oscillations is produced, or in the "off" position shown at which only one of the oscillating circuits 184 and 186 can be used at one time. The output range switch 191 is placed in either the position shown or in its other position. The cable end assembly 53 (FIG. 2) is mounted inside the cable connector receptacle 42. The main on-off switch 126 is turned on, and the electrode 19 is moved to a position adjacent or touching tissues of the patient 21 (FIG. 1) at a point where electrosurgery is to be performed. The appropriate one of the foot operated switches 196 and 198 (FIG. 9) is moved to its other position to provide a radio frequency current flow in the coil 28 which induces a like radio frequency oscillation in the coil 26. As the electrode 19 touches or approaches the body of the patient, an electrosurgical action is provided at the electrode, and a return electrical path is provided through the ancillary or passive electrode 22.

When the electrosurgical operation is to be an ordinary or usual cutting action, the blend switch 2341 is disposed in the position shown ("off" position), and the foot operated switch 198 is moved to its other position to set the oscillating circuit 186 in operation and to provide an uninterrupted oscillation. If a coagulating, dessicating, or fulgurating action is desired, the foot operated switch 196 is moved to its other position to cause operation of the oscillating circuit 184 and the multivibrator circuit of the transistors 244 and 246 providing an interrupted oscillation. If a blend of interrupted and uninterrupted oscillations is required, as where very substantial tissue destruction is desired as in some cutting operations, the blend switch 2341 is moved to its other or "on" position, and the switch 198 is moved to its other position to cause delivery of a blending of interrupted and uninterrupted oscillations.

The power delivered by the oscillating circuit 184 can be adjusted by movement of the tap of the potentiometer 201. The power delivered by the oscillating circuit 186 can be adjusted by movement of the tap of the potentiometer 203.

The condenser 227 (FIG. 10), through which the passive electrode 22 is coupled to ground, permits passage of radiofrequency current to permit electrosurgical action but limits passage of lower frequency current which might shock the patient. The condenser 49, through which the driver coil 28 is coupled to ground, similarly permits passage of radiofrequency current but prevents passage of lower frequency current generated as a sub-harmonic of the radiofrequency current to isolate the coils 28 and 26 from such lower frequency current. The condenser 49 is disposed in the handpiece to isolate the driver coil 28 from the outer conductor 68 of the coaxial cable 18 shield, which is at ground potential.

With the structure of this invention, a number of probe or handpiece elements can be employed with a single power unit and cable 18, and change of handpiece elements can be rapidly and conveniently effected.

The electrosurgical device described above and illustrated in the drawings is subject to structural modification without departing from the spirit and scope of the appended claims.

Having described my invention, what I claim as new and desire to secure by letters patent is:

1. In an electrosurgical device, means for generating a radio-frequency electrosurgical current, a handpiece, means on the handpiece for holding an electrosurgical instrument, a passive electrode coupled to the generating means to provide return from a patient and a circuit connecting the generating means to the instrument holding means which comprises a plurality of condensers connected in series between the generating means and the instrument holding means and inductance means connected between successive condensers and ground, the inductance means discharging non-radio-frequency current to ground in the event of condenser failure.

2. In an electrosurgical device, the combination of means for generating a radio-frequency potential between an output lead and a ground, a handpiece, means on the handpiece for holding an electrosurgical instrument, a passive electrode coupled to the generating means to provide return from a patient and a circuit connecting the output lead and the instrument holding means which comprises a plurality of condensers connected in series between the output lead and the instrument holding means, and inductance means connected between successive condensers and the ground, the inductance means discharging non-radio-frequency current to ground in the event of condenser failure.

3. An electrosurgical device as in claim 2 wherein there are at least three condensers connected in series in the circuit connecting the output lead and the instrument holding means and at least two inductance means.

4. In an electrosurgical device, means for generating a radio-frequency electrosurgical current, a handpiece, means on the handpiece for holding an electrosurgical instrument, a passive electrode coupled to the generating means to provide return from a patient and a circuit connecting the generating means to the instrument holding means which includes in its output a grounding means to discharge non-radio-frequency current to ground should radio-frequency coupling circuits electrically fail in the output of the device.

* * * * *